United States Patent [19]

Anaebonam et al.

[11] Patent Number: 5,763,449
[45] Date of Patent: Jun. 9, 1998

[54] PLEASANT-TASTING AQUEOUS LIQUID COMPOSITION OF A BITTER-TASTING DRUG

[75] Inventors: Aloysius O. Anaebonam, Burlington; Emmett Clemente, Manchester; Abdel A. Fawzy, Groton, all of Mass.

[73] Assignee: Ascent Pediatrics, Inc., Wilmington, Mass.

[21] Appl. No.: 692,081

[22] Filed: Aug. 7, 1996

[51] Int. Cl.$^6$ .................... A61K 31/505; A61K 31/56; A61K 31/16; A61K 31/075

[52] U.S. Cl. .................... 514/275; 514/179; 514/629; 514/718

[58] Field of Search .................... 514/718, 275, 514/179, 629

[56] References Cited

U.S. PATENT DOCUMENTS

| | | | |
|---|---|---|---|
| 2,909,522 | 10/1959 | Hitchings et al. | 260/256.4 |
| 4,303,643 | 12/1981 | Armstrong | 424/80 |
| 4,393,200 | 7/1983 | Miyashita et al. | 536/18.1 |
| 5,154,926 | 10/1992 | Kawasaki et al. | 424/439 |
| 5,455,049 | 10/1995 | Anaebonam et al. | 424/499 |

OTHER PUBLICATIONS

Dhabhar, D.J., WPIDS abstract, AN 95-269254 [35], (1995).

Budavari, Susan, ed., *The Merck Index*, 11$^{th}$ Ed., Merck & Co., Inc. (Rahway, NJ: 1989), pp.132, 1321.

Horn et al., *J. Pharm. Sci.*, 71(9):1021-1026 (1982).

Bühler, *Kollidon*, BASF, Ak,tiengesellshaft, Ludwigshafen, Germany, pp. 39-42, 70-72, 113-115 (Aug., 1992).

Gennaro, Alfonso R., ed., *Remington's Pharmaceutical Sciences*, 18th ed., Mack Publishing Company (Easton, Pennsylvania: 1989), pp. 1290-1296.

*Primary Examiner*—William R. A. Jarvis
*Attorney, Agent, or Firm*—Welsh & Katz, Ltd.

[57] ABSTRACT

A liquid pharmaceutical composition is contemplated that comprises a pharmaceutically effective amount of a bitter tasting drug dissolved or dispersed in an aqueous medium that is free of ethanol. That aqueous medium consists essentially of water, about 5 to about 30 weight percent polyvinylpyrrolidone, about 45 to about 55 weight percent of a $C_3$–$C_6$ polyol, about 0.01 to about 0.5 weight percent ammonium glycyrrhizinate and one or more flavorants. The liquid composition is transparent and has a pleasant taste.

13 Claims, No Drawings

PLEASANT-TASTING AQUEOUS LIQUID COMPOSITION OF A BITTER-TASTING DRUG

TECHNICAL FIELD

This present invention relates to a liquid drug composition, and more particularly to a pleasant-tasting aqueous liquid pharmaceutical composition that contains an otherwise bitter-tasting drug.

BACKGROUND ART

Many useful, effective drugs have a bitter taste when dissolved in liquid form or even when administered as pills or tablets. Exemplary of such drugs are acetaminophen, terfenadine, guaifenesin, trimethoprim, prednisolone, ibuprofen, prednisolone sodium phosphate, methacholine, neostigmine, epinephrine, albuterol, pseudoephedrine hydrochloride, diphenhydramine, chlorpheniramine maleate, phenothiazine, chlorpromazine, chlordiazepoxide, amitriptyline, barbiturates, diphenylhydantoin, caffeine, morphine, demerol, codeine, lomotil, lidocaine, salicylic acid, sulfonamides, chloroquine and penicillins. These and other bitter-tasting drugs are consequently usually formatted for oral administration as coated pills or tablets or as a powder or prills within a capsule so that the bitter-tasting medicament does not contact the tongue during oral administration.

Although provision in an above coated tablet or pill form or within a capsule overcomes the problem of offensive taste for several valuable medicaments for most of the adult population that uses those drugs, many adults and many children have difficulty swallowing the pills or tablets or cannot swallow them, and thereby do not benefit from those drugs. Recently issued U.S. Pat. No. 5,455,049 illustrates one technique that was successful in overcoming the bitter taste problem associated with orally administered terfenadine.

The disclosure that follows illustrates another, more general solution to both of the problems of bitter taste and oral administration of a solid dosage form such as a pill or capsule that is applicable to adults and children that have difficulty swallowing or cannot swallow pills, capsules and the like, as well as an alternative delivery mode for the general population.

BRIEF SUMMARY OF THE INVENTION

A transparent liquid pharmaceutical composition is contemplated by the present invention. That composition comprises a pharmaceutically effective amount of a bitter-tasting drug that is dissolved or dispersed in an aqueous medium that is free of ethanol. That aqueous medium consists essentially of water, about 5 to about 30 weight percent polyvinylpyrrolidone (PVP), about 45 to about 55 weight percent of a $C_3$–$C_6$ polyol, about 0.01 to about 0.5 weight percent ammonium glycyrrhizinate and one or more flavorants. The aqueous liquid composition is transparent and has a pleasant taste; i.e., it is free from having a bitter taste that would otherwise be associated with the bitter-tasting drug.

In preferred practice, the drug is present in an amount of about 0.5 to about 5 weight percent and the ammonium glycyrrhizinate is present in a weight ratio relative to the drug of about 1:50 to about 1:10. More preferably, the PVP is present at about 7 to about 15 weight percent, the drug at about one to about 3 weight percent, with the glycyrrhizinate present at the before-noted weight ratio to the drug, and most preferably at a weight ratio to the drug of about 1:20.

The present invention has several benefits and advantages.

One benefit is that a contemplated composition has a pleasant taste that permits it to be administered to children without the usually observed reluctance of children to take the bitter-tasting drug.

An advantage of the invention is that the bitter drug-containing composition is provided as a liquid to that it can be taken by those persons that have difficulty swallowing or cannot swallow usual solid forms of the drug such as a pill, tablet or capsule.

Another benefit of the invention is that a contemplated composition is free of ethanol so that it can be taken by children to whom an ethanol-containing pharmaceutical composition would normally not be given.

Another advantage of the invention is that a contemplated composition is transparent, homogeneously dispersed and non-settling so that one need not resuspend the medication within the composition prior to each administration and each dose contains a desired amount of the medicament.

Still further benefits and advantages of the invention will be apparent to those skilled in the art from the disclosure that follows.

DETAILED DESCRIPTION OF THE INVENTION

The present invention contemplates a liquid pharmaceutical composition that contains a normally bitter-tasting drug as active ingredient. A contemplated composition nonetheless has at least a pleasant taste if not a good taste.

The otherwise or normally bitter-tasting drug is dissolved or dispersed in an aqueous medium that is transparent. That is, the composition of drug and ingredients other than the flavorant, even if not forming a true solution, is not cloudy or milky in the aqueous medium. It is presently not known if the aqueous medium containing the drug and other ingredients is a true solution or a non-settling dispersion, but that composition containing its various constituents discussed hereinafter is transparent as would be a true solution or a colloidal dispersion.

A contemplated pharmaceutical composition is free of ethanol (ethyl alcohol). Ethanol is often used in aqueous medicinal compositions as a solvent for the active medicament. However, because of its potential effects upon children, ethanol is not utilized in a contemplated composition, or if used is present in an amount of about one percent by volume or less.

A contemplated composition is referred to as having an aqueous medium in that water is present as a major ingredient.

A pharmaceutically effective amount of a bitter-tasting drug is also present in a contemplated composition as the active ingredient. Exemplary bitter-tasting drugs include acetaminophen, terfenadine, guaifenesin, trimethoprim, prednisolone, ibuprofen, prednisolone sodium phosphate, methacholine, neostigmine, epinephrine, albuterol, pseudoephedrine hydrochloride, diphenhydramine, chlorpheniramine maleate, phenothiazine, chlorpromazine, chlordiazepoxide, amitriptyline, barbiturates, diphenylhydantoin, caffeine, morphine, demerol, codeine, lomotil, lidocaine, salicylic acid, sulfonamides, chloroquine and penicillins. The determination of a bitter taste is carried out by standard, well-known practices, and is a characteristic often listed along with a description of the drug in texts such as The *Merck Index*, 11th ed., S. Budavari et al. eds., Merck & Co., Inc., Rahway, N.J. (1989) and *Remington's Pharmaceutical Sciences*, 18th ed., A. Gennaro ed., Mack Publishing Co., Easton, Pa. (1990).

A pharmaceutically effective amount of a bitter-tasting drug is a concentration of the drug, which when present in a predetermined volume of the composition, provides a therapeutic dosage. It should be apparent that a pharmaceutically effective amount of a bitter-tasting drug is or can be different for each drug. In addition, that amount can also differ for the same drug where compositions formulated for children and adults are contemplated.

Therapeutic dosages of a contemplated bitter-tasting drug are well-known and are available from the above-noted texts as well as from the *Physicians' Desk Reference*, Medical Economics Company, Inc., Oradell, N.J. or *Goodman and Gilman's* The Pharmacological Basis of Therapeutics, 8th ed., Gilman et al. eds, McGraw Hill, Inc., New York, N.Y. (1993). Exemplary therapeutic dosages and therapeutically effective amounts of exemplary bitter-tasting drugs are provided hereinafter.

Exemplary amounts of active bitter-tasting drug are present at about 0.1 to about 10 weight percent, and preferably at about 0.5 to about 5 weight percent of the completed composition. The bitter-tasting drug is more preferably present at about one to about 3 weight percent of the completed composition.

In addition to the water and bitter-tasting drug, a contemplated composition also contains about 5 to about 30 weight percent polyvinylpyrrolidone, (PVP) and preferably about 7 to about 15 weight percent PVP. PVP is commercially available from a number of suppliers under a number of designations. The PVPs sold under the Trademark KOLLIDON® K25, K30 and K90 having weight-average molecular weights of 28,000–34,000, 44,000–54,000 and 1,000,000–1,500,000, respectively, are preferred for use here, with the K25 and K30 being most preferred.

PVP is dissolved or dispersed in the water of the aqueous medium and serves to assist in dissolving or dispersing the bitter-tasting drug in that medium, as well as masking the flavor of the bitter-tasting drug. The disclosures of Volker B ühler's book, *Kollidon*, BASF Aktiengesellshaft, Ludwigshafen, Germany (1992) teach the use of PVP as both a solubilization aid for several drugs as well as for masking the bitter taste of acetaminophen. An exemplary formulation for an oral PVP- and acetaminophen-containing composition is provided at page 113, Table 81 of the above Bühler text, but to the inventors' knowledge, no commercial liquid product takes advantage of that combination of ingredients and effects, indicating that those debittering effects are insufficient to provide a useful product.

A contemplated composition also contains about 45 to about 55 weight percent (as solids or non-volatile liquids) of a $C_3$–$C_6$ polyol. Exemplary $C_3$–$C_6$ polyols include propylene glycol, glycerin (glycerol), threose, threitol, erythrose, erythritol, ribose, arabinose, lyxose, sorbitol, sorbose, glucose, mannose, galactose, xylose, fructose and the like.

A $C_3$–$C_6$ polyol serves the dual function of being a solvent for the system as well as being a bitter flavor masking agent. In one preferred embodiment, a mixture of two or more $C_3$–$C_6$ polyols is utilized. Such a preferred mixture utilizes a $C_3$ polyol such as glycerin or 1,3-propanediol (propylene glycol) and one or more $C_6$ polyols such as maltitol NF (a starch hydrolyzate containing about 75 weight percent dry solids of which at least about 50 percent is D-maltitol and about 15 percent or less is D-sorbitol and is available under the mark LYCASIN™ from Roquette Corp., Gurnee, Ill., fructose such as that available under the mark KRYSTAR™, from A. E. Staley Mfg. Co., Decatur, Ill. that is sold as an aqueous liquid about 77 weight percent of which is fructose, as well as sugars such as glucose, xylitol and the like. It is noted that each maltitol molecule is composed of a plurality of $C_6$ polyols linked together and so is deemed to be a $C_3$–$C_6$ polyol as is sucrose. This mixture, when utilized, is typically present at a ratio weight of 1:4 to about 3:5, $C_3$ to $C_6$ polyol, as non-volatiles. In another preferred embodiment, polyols other than a $C_6$ polyol constitute less than about 5 weight percent of the total composition.

Surprisingly, the use of the above $C_3$–$C_6$ polyols together with the PVP is not sufficient to suitably mask the bitter taste of the bitter-tasting drug. This fact remains even when further sweeteners such as sodium saccharin USP present at 0.05–2 weight percent or aspartame present at about 0.1 to about 2 weight percent and further flavorants are admixed with the composition. A further debittering agent is still required to be present.

That further debittering agent is found to be ammonium glycyrrhizinate that can be present at about 0.01 to about 0.5 weight percent as ammonium glycyrrhizinate itself. The ammonium glycyrrhizinate is present at a weight ratio to the otherwise bitter-tasting drug of about 1:50 to about 1:10, and most preferably at weight ratio of about 1:20 ammonium glycyrrhizinate to drug.

Ammonium glycyrrhizinate is available as a 10 weight percent solution in glycerin or propylene glycol from MacAndrews & Forbes Company of Camden N.J. under the name MAGNASWEET® MM110 or MM115, and also as a white, amorphous powder as MM150. Ammonium glycyrrhizinate is the monoammonium salt of a triterpenoid saponin that consists of an aglycone of glycyrrhetic acid and a sugar moiety of two glucuronic acid units linked to each other. This material is said by its manufacturer to be about 50 to about 100 times sweeter than sucrose, and is known to be useful in masking bitterness.

Although ammonium glycyrrhizinate is a known bitterness-masking agent as is PVP, neither material alone or with the before-discussed sweeteners and flavorants is sufficient to mask the bitter taste of a contemplated bitter-tasting drug. Rather, PVP and ammonium glycyrrhizinate appear to potentiate each other to provide the desired bitterness-masking effect.

The mechanism by which the bitterness-masking is achieved is unknown. However, without wishing to be bound by theory, it is believed that a complex is formed between the PVP, drug and ammonium glycyrrhizinate, particularly because so little of the glycyrrhizinate is present.

The before-mentioned Bühler, *Kollidon*, BASF Aktiengsellshaft, Ludwigshafen, Germany (1992) book teaches that PVP forms complexes with aromatic compounds, particularly those drugs also having hydrophilic groups that can form hydrogen bonds such as carboxyl, hydroxyl and amine groups. See also, Horn et al., *J. Pharm. Sci.*, 71:1021–126 (1982). The contemplated bitter-tasting drugs have one or more rings, most of which are aromatic, and so it is thought that PVP forms a complex with the bitter-tasting drug. Table 20 at page 40 of Bühler's book lists interaction constants for several such complexes, although no such interaction constant could be determined for trimethoprim, which is quite useful here. See also, Horn et al., *J. Pharm. Sci.*, 71:1021–1026 (1982).

Ammonium glycyrrhizinate contains no aromaticity, but has several hydrophilic groups such as hydroxyls and carboxyl groups and a hydrophobic aglycone portion that can be solvated by the PVP polymeric backbone. It is consequently believed that the three components form a presently undefined complex in the aqueous medium, and that that complex acts to shield taste buds from the bitterness inherently present in the bitter-tasting drug.

As was noted previously, a contemplated composition can also contain additional sweeteners, and flavorants, as well as colorants and thickeners. Flavorants such as bubble gum and chocolate flavors can provide opacity or translucency to a contemplated composition, while the composition other than the flavorant is transparent. Exemplary thickeners include sodium alginate, gelatin or a polyalkylene oxide such as the polyoxyethylene-polyoxypropylene-polyethylene terpolymer available under the name PLURONIC® F68 having an average of 75 polymerized ethylene oxide units on either side of 30 polymerized propylene oxide units, F-87 having 62 polymerized ethylene oxide units on either side of 39 polymerized propylene oxide units, or F-88 having an average of about 97 polymerized ethylene oxide groups on either side of about 39 polymerized propylene oxide groups that are available from BASF, Mount Olive, N.J. Conventional preservatives such as sodium benzoate NF, methylparaben NF and propylparaben NF can be and preferably are also present. A contemplated aqueous liquid pharmaceutical composition has a viscosity of 25° C. between that of water and about that of corn syrup at 25° C.

A contemplated composition has a final pH value of about 2 to about 8, and preferably about 3 to about 5, and more preferably about 3.5 to about 4.5. Sodium hydroxide (1N) and hydrochloric acid (10N) or citric acid and sodium citrate are typically used for pH value adjustments and maintenance.

A contemplated aqueous liquid pharmaceutical composition is readily prepared. Thus, in an exemplary procedure where a $C_3$ polyol is utilized, a solution or dispersion of about 30 weight percent PVP is prepared in water. About one part bitter-tasting drug is slurried with about 5 parts by weight $C_3$ polyol (glycerin or propylene glycol or both). The two compositions are admixed and heated to a temperature of about 45° C. with continued agitation. Agitation is continued at that temperature until a clear, non-settling solution or dispersion is formed, which generally takes about 30 minutes. Where no or less than 5 weight percent $C_3$ polyol is used, the bitter-tasting drug is admixed directly with the aqueous PVP.

The aqueous composition so formed is cooled at a temperature below about 30° C. and the ammonium glycyrrhizinate, other $C_3$–$C_3$ polyols, flavorants, colorant if used and remaining ingredients are admixed until a homogenous composition is obtained. These additions are typically carried out serially, with admixture to homogeneity between each admixture. The pH value is thereafter adjusted as required. The examples that follow illustrate these procedures more fully.

BEST MODE FOR CARRYING OUT THE INVENTION

EXAMPLE 1

Guaifenesin-Containing Syrup

A liquid anti-tussive composition was prepared containing the following ingredients and their amounts.

| Ingredient | Amount |
| --- | --- |
| Guaifenesin, USP | 2.0 g |
| Polyvinylpyrrolidone (PVP;K25) | 7.5 g |
| Glycerin, USP | 10.0 g |
| Purified Water, USP | 25.0 mL |
| Sodium Benzoate, NF | 0.15 g |
| Saccharin Sodium, USP | 0.50 g |
| Monoammonium Glycyrrhizinate (10%)[1] | 1.0 g |
| Citric Acid anhydrous, USP | 0.25 g |
| Sodium Citrate, USP | 0.384 g |
| Sodium Alginate, USP | 0.2 g |
| Maltitol Syrup, NF (75%) solids) | 20.0 g |
| Flavors and Colorants | q.s. |
| Liquid Fructose | q.s. |
| (77.0–77.5% solids) | 100.0 mL |

[1] A 10% solids solution in glycerin or propylene glycol from MacAndrews & Forbes Co.

The PVP was dissolved or dispersed in 25 mL of purified water. The sodium alginate was added to that composition and the resulting admixture mixed until homogeneity to form Phase A.

The guaifenesin and glycerin were mixed to form a smooth slurry as Phase B. Phase A was then added to Phase B with constant stirring. This admixture was heated to a temperature of 45° C. and that temperature was maintained for about 30 minutes with mixing to form Phase C as a transparent composition. Phase C was then cooled to a temperature below 30° C.

The citric acid and sodium citrate were dissolved in 5 mL of water to form Phase D. The sodium benzoate and sodium saccharin were similarly dissolved in another 5 mL of water to form Phase E.

Phase D was admixed with Phase C and mixed for about 5 minutes to obtain homogeneity. Phase E was then similarly admixed with that homogeneous composition to form Phase F.

The maltitol was similarly admixed with Phase F to form Phase G to which the ammonium glycyrrhizinate was added with another about 5 minutes mixing time being used. The flavors and colorants were then admixed, with a mixing time of about 5 minutes, followed by addition of a sufficient amount of liquid fructose to make the desired volume and mixing to homogeneity. The pH value was thereafter adjusted to be between 4 and 5 using a citric acid or sodium citrate solution. This composition provides 100 mg of guaifenesin per 5 mL (teaspoon).

Four differently flavored and colored clear syrups were prepared using the before-described ingredients. Those syrups were orange/vanilla-flavored colorless, vanilla-flavored colorless, chocolate-flavored brown, and gum-fruit-flavored red syrups. The bitter guaifenesin taste was well masked in each syrup.

EXAMPLE 2

Comparative Taste Study

A flavor acceptance study was conducted using a composition of Example 1 colored red and flavored with gum-fruit and a commercially available guaifenesin-containing composition sold under the mark ROBITUSSIN®. Eighty-one children aged between 3 and 6 years (33 boys and 48 girls) were enrolled in the study.

More specifically, the study followed a two-way cross-over design, with all subjects evaluating both products at one-half teaspoon for each product. The two products were evaluated on a single study day. The sequence of products was randomized among subjects. All enrolled subjects completed all aspects of the study protocol. There were no adverse events reported.

The primary analysis of the ordinal taste scores (1=disliked a lot, 2=disliked a little, 3=just OK, 4=liked a little, 5=liked a lot) was an analysis of variance including factors for dosing sequence, subject within sequence, dose order and product. The effect of sequence was tested using subject (sequence) for error and was not significant. Dose order and product effects were tested against the residual error variance. All tests were performed at the 5% level. A secondary analysis tested product preferences using the Sign Test.

The results showed a statistically significant preference (p=0.013) for a syrup of Example 1 (mean=3.42±1.52) compared to ROBITUSSIN® (mean=2.86±1.63) based on the primary analysis of the children's ordinal ratings of the flavor. In the secondary analysis, 59.3 percent of children (48/81) stated a preference of the syrup of Example 1 compared to ROBITUSSIN® (33/81), showing a trend in support of the primary results.

The analysis of variance showed no statistically significant effect of sequence. Dose order, however, did show a statistically significant effect (p=0.004) on flavor scores: the second product tasted tended to be rated higher than the first. Thus, mean flavor scores±standard deviations were 3.03±1.56 for the composition of Example 1 when tested first and 3.80±1.38 when tested second for an overall score of 3.42±1.52. The commercial ROBITUSSIN® product exhibited scores of 2.61±1.70 and 3.13±1.54 when tested first and second, respectively, and an overall score of 2.86±1.63.

EXAMPLE 3
Trimethoprim Oral Liquid #1

An oral liquid pharmaceutical composition was prepared utilizing the following ingredients in the following amounts.

| Ingredient | Amount |
| --- | --- |
| Trimethoprim, USP | 5 kg |
| Polyvinylpyrrolidone, USP (PVP;K25) | 50 kg |
| Glycerin, USP | 25 kg |
| Propylene Glycol, USP | 52.5 kg |
| Purified Water, USP | 125 kg |
| Methylparaben, NF | 500 g |
| Propylparaben, NF | 250 g |
| Sodium Benzoate, NF | 500 g |
| Saccharin Sodium, USP | 5 kg |
| Monoammonium Glycyrrhizinate (10% solids)[1] | 20 kg |
| Sorbitol Solution, USP | 65 kg |
| Hydrochloric Acid, NF | 1.25 L |
| Sodium Hydroxide, USP (1N) | q.s. |
| Hydrochloric Acid, USP (10N) | q.s. |
| Maltitol Solution, NF (75%) solids) | 50 kg |
| Bubblegum Flavor | 2.5 kg |
| Liquid Fructose | q.s. |
| (77.0–77.5% solids) | |
| | 500 L |

[1]A 10% solids solution in glycerin or propylene glycol from MacAndrews & Forbes Co.

Here, 110 kg of the purified water was acidified with 1.25 liters of HCl to which the trimethoprim was added and mixed until dissolved. The PVP was admixed with agitation and the agitation continued until a homogeneous, clear composition was obtained. Most of the propylene glycol (40 kg) was admixed to homogeneity, followed by admixture of the glycerin. The resulting admixture was heated to a temperature of 45° C. and maintained of that temperature with constant mixing for about 10 minutes to form Phase A.

The parabens were dissolved in the remaining 12.5 kg of propylene glycol to form Phase B. The sodium benzoate and sodium saccharin were dissolved in 15 kg of purified water to form Phase C.

The maltitol was admixed with Phase A for about 5 minutes, at which time the sorbitol was added followed by another about 5 minutes of stirring to form Phase D. Phase B was admixed with Phase D followed by about 5 minutes of stirring to form Phase E, to which Phase C was added and mixed for about 5 minutes to form Phase F. The ammonium glycyrrhizinate was admixed with Phase F followed by about 5 minutes of stirring to form Phase G to which the bubblegum flavor was added and stirred to homogeneity. The volume was made up to 500 liters with the liquid fructose, and the resulting composition was stirred to homogeneity. The pH value of the composition was thereafter adjusted with sodium hydroxide and/or hydrochloric acid as required to provide a pH value of 3.5 to 4.5.

The resulting liquid pharmaceutical composition did not have the bitter taste usually associated with trimethoprim, and provided trimethoprim in an amount of 50 mg/teaspoon (50 mg/5 mL).

EXAMPLE 4
Trimethoprim Oral Liquid #2

A second trimethoprim-containing oral liquid pharmaceutical composition was prepared that contained less than 5 weight percent $C_3$ polyol; i.e., only the $C_3$ polyol contributed by an ammonium glycyrrhizinate solution. That composition had the following ingredients present in the following amounts.

| Ingredient | Amount |
| --- | --- |
| Trimethoprim, USP | 1.0 g |
| Polyvinylpyrrolidone, USP (PVP;K25) | 15.0 g |
| Purified Water, USP | 25 mL |
| Sodium Benzoate, NF | 0.15 g |
| Saccharin Sodium, USP | 1.0 g |
| Monoammonium Glycyrrhizinate (10% solids)[1] | 4.0 g |
| Hydrochloric Acid, NF | 0.25 mL |
| Sodium Hydroxide, USP (1N) | q.s. |
| Hydrochloric Acid, USP (10N) | q.s. |
| Maltitol Solution, NF (75%) solids) | 10 g |
| Flavorant | q.s. |
| Colorant | q.s. |
| Liquid Fructose | q.s. |
| (77.0–77.5% solids) | |
| | 100.0 mL |

[1]A 10% solids solution in glycerin or propylene glycol from MacAndrews & Forbes Co.

For this preparation, the purified water was acidified with the 0.25 mL of hydrochloric acid. The trimethoprim was added to the acidified water with stirring over about 5 minutes. The PVP was then added with stirring to homogeneity for about 10 minutes, followed by admixture of the maltitol and stirring for a further 5 minutes time period. The resulting admixture was then heated to a temperature of 45°–60° C. and maintained at that temperature with continued mixing until the composition clarified and no particles could be seen. The heating was then stopped, the composition cooled to below 30° C., and ammonium glycyrrhizinate was added. The composition was then mixed for about 5 minutes to form Phase A.

The sodium benzoate and sodium saccharin were dissolved in about 30 g of liquid fructose to form Phase B. Phase B was added to Phase A, and the resulting composition was mixed for about 5 minutes, after which the flavorant and colorant were added with another 5 minutes of mixing. The pH value was adjusted to 3.5–4.5, the composition was made up to a final volume of 100 mL using liquid fructose, and the resulting composition was stirred for another 5 minutes to form the trimethoprim-containing oral liquid pharmaceutical composition. That composition was homogeneous and clear, and exhibited a pleasant taste, particularly as compared to the usually bitter taste of trimethoprim, and provided 50 mg of trimethoprim/5 mL of composition.

The foregoing description and the examples are intended as illustrative and are not to be taken as limiting. Still other variations within the spirit and scope of this invention are possible and will readily present themselves to those skilled in the art.

What is claimed is:

1. A liquid pharmaceutical composition comprising a pharmaceutically effective amount of a bitter-tasting drug dissolved or dispersed in an aqueous medium that is free of ethanol, said aqueous medium consisting essentially of water, about 5 to about 30 weight percent polyvinylpyrrolidone, about 45 to about 55 weight percent of a $C_3$–$C_6$ polyol, about 0.01 to about 0.5 weight percent ammonium glycyrrhizinate and one or more flavorants, said liquid composition being transparent and having a pleasant taste when administered orally.

2. The liquid pharmaceutical composition according to claim 1 wherein said polyvinylpyrrolidone is present at about 7 to about 15 weight percent.

3. The liquid pharmaceutical composition according to claim 1 wherein said $C_3$–$C_6$ polyol is present as a mixture of $C_3$ polyols and $C_6$ polyols.

4. The liquid pharmaceutical composition according to claim 1 wherein said ammonium glycyrrhizinate is present at a weight ratio to said drug of about 1:50 to 1:10.

5. The liquid pharmaceutical composition according to claim 1 wherein said drug is present in an amount of about 0.5 to about 5 weight percent.

6. A liquid pharmaceutical composition comprising about 0.5 to about 5 weight percent of a bitter-tasting drug dissolved or dispersed in an aqueous medium that is free of ethanol, said aqueous medium consisting essentially of water, about 7 to about 15 weight percent polyvinylpyrrolidone, about 45 to about 55 weight percent of a $C_3$–$C_6$ polyol, about 0.01 to about 0.5 weight percent ammonium glycyrrhizinate and one or more flavorants, said ammonium glycyrrhizinate being present at a weight ratio to said drug of about 1:50 to about 1:10 and said liquid composition being transparent and having a pleasant taste when administered orally.

7. The liquid pharmaceutical composition according to claim 6 wherein said $C_3$–$C_6$ polyol is present as a mixture of $C_3$ polyols and $C_6$ polyols.

8. The liquid pharmaceutical composition according to claim 7 wherein the weight ratio of said $C_3$ polyol to said $C_6$ polyol is about 1:4 to about 3:5.

9. The liquid pharmaceutical composition according to claim 6 wherein polyol other than a $C_6$ polyol constitutes less than about 5 weight percent of said composition.

10. The liquid pharmaceutical composition according to claim 6 wherein said drug is present in an amount of about one to about 3 weight percent.

11. The liquid pharmaceutical composition according to claim 6 wherein said bitter tasting drug is selected from the group consisting of acetaminophen, terfenadine, guaifenesin, trimethoprim, prednisolone, ibuprofen, prednisolone sodium phosphate, methacholine, neostigmine, epinephrine, albuterol, pseudoephedrine hydrochloride, diphenhydramine, chlorpheniramine maleate, phenothiazine, chlorpromazine, chlordiazepoxide, amitriptyline, barbiturates, diphenylhydantoin, caffeine, morphine, demerol, codeine, lomotil, lidocaine, salicylic acid, sulfonamides, chloroquine and penicillins.

12. The liquid pharmaceutical composition according to claim 6 wherein said bitter tasting drug is guaifenesin.

13. The liquid pharmaceutical composition according to claim 6 wherein said bitter tasting drug is trimethoprim.

* * * * *